(12) United States Patent
Kuhara et al.

(10) Patent No.: US 7,629,316 B2
(45) Date of Patent: Dec. 8, 2009

(54) METHOD FOR PROLIFERATING NATURAL KILLER CELLS

(75) Inventors: Tetsuya Kuhara, Zama (JP); Takehito Itoh, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 0 days.

(21) Appl. No.: 12/179,898

(22) Filed: Jul. 25, 2008

(65) Prior Publication Data

US 2008/0287365 A1 Nov. 20, 2008

Related U.S. Application Data

(62) Division of application No. 10/573,564, filed as application No. PCT/JP2005/016449 on Sep. 7, 2005, now abandoned.

(30) Foreign Application Priority Data

Sep. 15, 2004 (JP) ............................. 2004-268041

(51) Int. Cl.
*A61K 38/00* (2006.01)
*C12N 5/00* (2006.01)
*C12N 5/02* (2006.01)

(52) U.S. Cl. .......................... 514/12; 435/325

(58) Field of Classification Search ........................ None
See application file for complete search history.

(56) References Cited

FOREIGN PATENT DOCUMENTS

| EP | 1 790 355 | 5/2007 |
|---|---|---|
| JP | 2001-503430 | 3/2001 |
| JP | 2001-149069 | 6/2001 |
| JP | 2002-515893 | 5/2002 |
| WO | WO 98/19675 | 5/1998 |
| WO | WO 98/33509 | 8/1998 |
| WO | WO 02/47612 | 6/2002 |

OTHER PUBLICATIONS

Teraguchi, et al. "Protection Against Infections by Oral Lactoferrin: Evaluation in Animal Models," *BioMetals*, vol. 17, No. 3, pp. 231-234, 2004.
Sivori, et al. "CpG and Double-Stranded RNA Trigger Human NK Cells by Toll-Like Receptors: Induction of Cytokine Release and Cytotoxicity Against Tumors and Dendritic Cells," *PNAS*, vol. 101, No. 27, 10116-10121, Jul. 6, 2004.
Decicco, et al. "All-*trans*-retinoic Acid and Polyriboinosinic: Polyribocytidylic Acid in Combination Potentiate Specific Antibody Production and Cell-Mediated Immunity," *Immunology*, vol. 104, No. 3, pp. 341-348, 2001.
Kasaian, et al. "Cyclosporin a Inhibition of Interleukin 2 Gene Expression, But Not Natural Killer Cell Proliferation, After Interferon Induction In Vivo," *Journal of Experimental Medicine*, vol. 171, pp. 745-762, 1990.
Kuhara, et al. "Oral Administration of Lactoferrin Raises NK Cell Activity in Mice," *Milk Science*, vol. 53, No. 4, pp. 262-264, 2004.
Riccardi, et al. "Generation of Mouse Natural Killer (NK) Cell Activity: Effect of Interleukin-2 (IL-2) and Interferon (IFN) on the In Vivo Development of Natural Killer Cells From Bone Marrow (BM) Progenitor Cells," *International Journal of Cancer*, vol. 38, pp. 553-562, 1986.
Tsuda, et al. "Inhibition of Carcinogenesis by Bovine Lactoferrin and Analysis of Mechanisms," *FFI Journal*, No. 200, pp. 27-35, 2002 (in Japanese).
Tsuda, et al. "Cancer Prevention by Bovine Lactoferrin and Underlying Mechanisms—A Review of Experimental and Clinical Studies," *Biochem. Cell Biol.*, vol. 80, pp. 131-136, 2002.
Wang, et al. "Activation of Intestinal Mucosal Immunity in Tumor-Bearing Mice by Lactoferrin" *Japanese Journal of Cancer Research*, vol. 91, pp. 1022-1027, Oct. 2000.
Porgador, et al. "Natural Killer Cell Lines Kill Autologous $\beta_2$-Microglobulin-Deficient Melanoma Cells: Implications for Cancer Immunotherapy," *Proc. Natl. Acad. Sci.*, USA, vol. 94, pp. 13140-13145, 1997.
Hemmi and Akira, *Molecular Medicine*, vol. 39, pp. 238-246, 2002.
Akira, S., *Molecular Medicine*, vol. 40, pp. 186-193, 2003.
Schmidt, et al. "APC-Independent Activation of NK Cells by the Toll-Like Receptor 3 Agonist Double-Stranded RNA," *The Journal of Immunology*, vol. 172, pp. 138-143, 2004.
Hébert, et al. "Ethanol Decreases Natural killer Cell Activation but Only Minimally Affects Anatomical Distribution After Administration of Polyinosinic:Polycytidylic Acid: Role in resistance to B16F10 Melanoma," *Alcoholism Clinical and Experimental Research*, vol. 27, No. 10, pp. 1622-1631, Oct. 2003.
Collier, et al. "Mechanisms of Suppression of Poly I:C-induced Activation of NK Cells by Ethanol," *Alcohol*, vol. 21, pp. 87-95, 2000.

(Continued)

Primary Examiner—Robert Landsman
(74) Attorney, Agent, or Firm—Knobbe, Martens, Olson & Bear, LLP

(57) ABSTRACT

Natural Killer (NK) cells are obtained by administering a Toll-like receptor ligand such as polyinosinic-polycytidylic acid into the peritoneal cavity of an animal to which lactoferrin has been administered to proliferate NK cells in the peritoneal cavity and collecting NK cells from the peritoneal cavity.

5 Claims, No Drawings

OTHER PUBLICATIONS

Kuhara, et al. "Oral Administration of Lactoferrin Increases NK Cell Activity in Mice via Increased Production of IL-18 and Type I IFN in the Small Intestine," *Journal of Interferon & Cytokine Research*, vol. 26, No. 7, pp. 489-499, Jul. 2006.

Shimizu, et al. "Lactoferrin-mediated Protection of the Host from Murine Cytomegalovirus Infection by a T-cell—dependent Augmentation of Natural Killer Cell Activity," *Archives of Virology*, vol. 141, No. 10, pp. 1875-1889, 1996.

Damiens, et al. "Effects of Human Lactoferrin on NK Cell Cytotoxicity Against Haematopoietic and Epithelial Tumour Cells," *Biochimica et Biophysica Acta*, vol. 1402, No. 3, pp. 277-287, Apr. 24, 1998.

Supplementary Partial European Search Report, dated Jun. 25, 2009.

METHOD FOR PROLIFERATING NATURAL KILLER CELLS

RELATED APPLICAITONS

This application is a divisional of U.S. application Ser. No. 10/573,564, filed Mar. 27, 2006 which is the U.S. National Phase under 35 U.S.C. § 371 of International Application PCT/JP2005/016449, filed Sep. 7, 2005, which was published in a non-English language and which claims priority to JP 2004-268041, filed Sep. 15, 2004.

TECHNICAL FIELD

The present invention relates to a drug and method for proliferating natural killer cells, a method for producing natural killer cells and a method for screening for a substance having a natural killer cell proliferating action. The present invention is useful in the fields of medicine, food and so forth.

BACKGROUND ART

Natural killer (NK) cells are a group of cells having a cytotoxic activity against various tumor cells, virus infected cells and cells having different major histocompatibility antigens, and their activation and inhibition are regulated primarily by receptors that recognize self and nonself.

NK cells are considered to have important functions as one type of lymphocytes involved in natural immunity. Against viral infection, in particular, they play a very important role in immune responses in early infection until acquired immunity is established by T lymphocytes and B lymphocytes.

That is, even if T lymphocytes and B lymphocytes are normal, immunodeficient patients and mice that are deficient in the natural killer function are very easily infected by specific viruses. In recent years, it has been revealed that receptors of NK cells recognize products of specific viruses.

Thus, attempts have been made to effectively utilize various functions of NK cells involved in tumor immunity for tumor treatment and removal of virus infected cells that are supposed to become a source of tumor.

As a method for obtaining NK cells from laboratory animals, a method of collecting cells from the spleen, blood, bone marrow and so forth and purifying them is known. However, since all of these tissues contain NK cells only in low proportions, technical skills and suitable equipment are required to secure NK cells necessary for experiments.

As for methods for producing or proliferating NK cells, it is well known that if peripheral blood mononuclear cells are cultured in a culture broth to which a large amount of interleukin-2 is added, lymphokine-activated killer lymphocytes (LAK cells) are proliferated within about 1 week in the case of human, and a large amount of NK cells are contained in this culture. Recently, a method has been developed which comprises irradiating cells of the human B cell strain 721.221, in which the major histocompatibility class I (MHC-I) is hardly expressed on the cell surfaces, with a radioactive ray so that the cells should lose division potential, culturing the cells with monocular cells in peripheral blood as mixed culture for 5 to 6 days, purifying NK cells from the culture and further continuing culture to obtain a large amount of NK cells (e.g., Non-patent document 1).

Further, a method for proliferating human NK cells comprising the step of mixed culture of peripheral blood mononuclear cells and cells of human fibroblast Wilms' tumor line HFWT (Patent document 1), a method for enhancing an activity of animal natural killer lymphocytes utilizing conjugated linoleic acids as an active ingredient (Patent document 2) and so forth have been disclosed. However, the technique disclosed in Patent document 1 is a method for proliferating human NK cells by mixed culture of peripheral blood mononuclear cells and cells of human fibroblast Wilms' tumor line HFWT, and any method for collecting NK cells proliferated in vivo and screening for a factor that enhances the natural killer activity are not disclosed in this document. Further, in Patent document 2, changes in killer lymphocytes enhanced by conjugated dienoic linoleic acids in the spleen was followed, and any method for collecting NK cells proliferated in vivo and screening for a factor that enhances the natural killer activity are not disclosed in this document.

At present, the most common method for measuring an activity of NK cells (natural killer activity, NK activity) is a method of observing a cytotoxic activity against human K562 cells or mouse lymphoma cell line Yac-1 by co-culturing a group of cells including Yac-1 cells radiolabeled with $^{51}$Cr or the like and measuring radioactivity released in the culture supernatant. Further, a method for measuring the NK activity in living bodies is a method of transplanting tumor cells radiolabeled in the same manner as mentioned above into a living body or infecting an animal with a virus or the like and observing the NK activity, and these methods require a special facility and equipment.

Lactoferrin is known as a lactoprotein having various actions such as an antibacterial action, immunity activating action and antitumor action. Lactoferrin is a milk-derived glycoprotein that is highly safe and can be continuously taken for a long period of time. Since lactoferrin itself has almost no taste or odor, it is a highly versatile protein as an additive for various food, drugs and feeds.

Patent document 3 (International Patent Publication in Japanese (Kohyo) No. 2002-515893) proposes a method for stimulating NK cells in a patient which comprises the step of administering a composition containing a modified human lactoferrin to the patient. However, Patent document 3 does not describe the effect of the modified human lactoferrin for actually stimulating NK cells, and its basis has been unclear.

The Toll-like receptors (TLR) recognize various components of bacteria and are believed to play an important role not only in recognition of bacteria in natural immunity but also in activation of acquired immunity, and also considered to have functions of recognizing various pathogenic components and inducing unique responses. Currently, the Toll-like receptor family in mammals consists of 10 family members, and pathogen-constituting components (ligands) recognized by each Toll-like receptor have been identified. These ligands, the pathogen-constituting components, include lipids, sugars, proteins, nucleic acids and so forth (Non-patent documents 2 and 3).

[Patent document 1] Japanese Patent Laid-open (Kokai) No. 2001-149069

[Patent document 2] International Patent Publication in Japanese (Kohyo) No. 2001-503430

[Patent document 3] International Patent Publication in Japanese (Kohyo) No. 2002-515893

[Non-patent document 1] Proc. Natl. Acad. Sci., USA, Vol. 94, 1997, pp. 13140-13145

[Non-patent document 2] Molecular Medicine, Vol. 39, 2002, pp. 238-246

[Non-patent document 3] Molecular Medicine, Vol. 40, 2003, pp. 186-193

DISCLOSURE OF THE INVENTION

An object of the present invention is to provide a technique of proliferating NK cells in vivo and a method for screening for a substance having an action of proliferating NK cells.

When the inventors of the present invention examined a method for screening for a food or drink-derived factor that enhances the NK activity, they administered lactoferrin, which is a food (milk)-derived factor, to an animal for a predetermined period, then administered a Toll-like receptor ligand with specific timing during the administration period, and found that the proportion of NK cells among the intraperitoneal cells markedly increased in the peritoneal cavity of the animal. Further, they found that since it became possible to induce NK cells in the peritoneal cavity by the aforementioned method, the NK activity could be easily analyzed and NK cells could be conveniently collected. Thus, they accomplished the present invention.

The first invention of the present application that achieves the aforementioned object is a drug for proliferating animal NK cells, which comprises a first agent containing lactoferrin and a second agent containing a Toll-like receptor ligand, wherein the first agent and the second agent are separately packaged in the drug. In preferred embodiments, the NK cell proliferating drug of the present invention is characterized by any of the following 1) to 3).

1) The aforementioned first agent is administered everyday for 5 to 10 days in an amount of 10 to 2000 mg/day/kg body weight in terms of the amount of lactoferrin, and the aforementioned second agent is administered 5 to 2 days before the completion of the administration of the first agent in an amount of 10 to 1000 μg/day/kg body weight in terms of the amount of the Toll-like receptor ligand.
2) The first agent containing lactoferrin is orally administered, and the second agent containing a Toll-like receptor ligand is intraperitoneally administered.
3) The aforementioned Toll-like receptor ligand is polyinosinic-polycytidylic acid (henceforth also referred to as "polyIC").

The second invention of the present application is a method for proliferating NK cells in an animal (except for human), which comprises administering lactoferrin and a Toll-like receptor ligand to the animal. In preferred embodiments, the NK cell proliferating method of the present invention is characterized by any of the following 4) to 6).

4) Lactoferrin is administered everyday for 5 to 10 days in an amount of 10 to 2000 mg/day/kg body weight, and the Toll-like receptor ligand is administered 5 to 2 days before the completion of the administration of lactoferrin in an amount of 10 to 1000 μg/day/kg body weight.
5) Lactoferrin is orally administered, and the Toll-like receptor ligand is intraperitoneally administered.
6) The aforementioned Toll-like receptor ligand is polyinosinic-polycytidylic acid.

The third invention of the present application is a method for producing NK cells, which comprises administering lactoferrin and a Toll-like receptor ligand to an animal (except for human), and collecting NK cells from the animal. In preferred embodiments, the method for producing NK cells of the present invention is characterized by any of the following 7) to 9).

7) Lactoferrin is administered everyday for 5 to 10 days to an animal (except for human) in an amount of 10 to 2000 mg/day/kg body weight, the Toll-like receptor ligand is administered 5 to 2 days before the completion of the administration of lactoferrin in an amount of 10 to 1000 μg/day/kg body weight, and NK cells are collected from the animal.
8) Lactoferrin is orally administered, the Toll-like receptor ligand is intraperitoneally administered, and NK cells are collected from the peritoneal cavity.
9) The aforementioned Toll-like receptor ligand is polyinosinic-polycytidylic acid.

The fourth invention of the present application is a method for screening for a substance having an action of proliferating NK cells in a living body of an animal (except for human), which comprises administering a test substance and a Toll-like receptor ligand to the animal and detecting induction of NK cells in the animal. In preferred embodiments, the screening method of the present invention is characterized by any of the following 10) to 13).

10) The test substance is administered everyday for 5 to 10 days to the animal (except for human), and the Toll-like receptor ligand is administered 5 to 2 days before the completion of the administration of the test substance.
11) The test substance is orally administered, and the Toll-like receptor ligand is intraperitoneally administered.
12) The Toll-like receptor ligand is polyinosinic-polycytidylic acid.
13) The test substance is food, drink or a component thereof.

The fifth invention of the present application is use of lactoferrin and a Toll-like receptor ligand in the production of a drug for proliferating animal natural killer cells, wherein the aforementioned drug for proliferating animal natural killer cells comprises a first agent containing lactoferrin and a second agent containing a Toll-like receptor ligand, and the first agent and the second agent are separately packaged in the drug. In preferred embodiments, the use of the present invention is characterized by any of the following 14) to 16).

14) The first agent is administered everyday for 5 to 10 days in an amount of 10 to 2000 mg/day/kg body weight in terms of the amount of lactoferrin, and the second agent is administered 5 to 2 days before the completion of the administration of the first agent in an amount of 10 to 1000 μg/day/kg body weight in terms of the amount of the Toll-like receptor ligand.
15) The first agent containing lactoferrin is orally administered, and the second agent containing a Toll-like receptor ligand is intraperitoneally administered.
16) The Toll-like receptor ligand is polyinosinic-polycytidylic acid.

BEST MODE FOR CARRYING OUT THE INVENTION

Hereafter, preferred embodiments of the present invention will be explained in detail. However, the present invention is not limited to the preferred embodiments described below, and can be freely modified within the scope of the present invention. In the present specification, percentage is used on mass basis unless otherwise indicated.

The animal NK cell proliferating drug of the present invention comprises a first agent containing lactoferrin and a second agent containing a Toll-like receptor ligand, wherein the first agent and the second agent are separately packaged in the drug.

As lactoferrin used for the present invention, there can be used commercially available lactoferrin and lactoferrin obtained from colostrum, transitional milk, normal milk or late lactation milk of mammals (e.g., human, cow, goat, sheep, horse and so forth) or processed products of these milks such as skimmed milk and whey as a raw material and isolated from the aforementioned raw materials by a conventional technique such as ion exchange chromatography. In particular, commercially available lactoferrin produced in an industrial scale (e.g., one produced by Morinaga Milk Industry Co., Ltd.) can be preferably used. Further, lactoferrin produced in microorganisms, animal cells, transgenic animals and so forth by using genetic engineering techniques can also be used. Further, modified lactoferrins, of which amino acid sequence is changed or modified, are also encompassed in the lactoferrin of the present invention so long as the NK cell proliferating action of lactoferrin is not degraded.

In the present invention, metal content in lactoferrin is not particularly limited, and there can be used any one type or a mixture of any two or more types selected from a group consisting of apolactoferrin obtained by deironizing lactoferrin with hydrochloric acid, citric acid or the like, metal-saturated lactoferrin with a saturation rate of 100% obtained by chelating the above-mentioned apolactoferrin with a metal such as iron, copper, zinc and manganese and partially metal-saturated lactoferrin to which a metal binds with various saturation rates lower than 100%.

As the Toll-like receptor ligand used for the present invention, any Toll-like receptor ligand can be used so long as the ligand recognizes one or more of the family members of Toll-like receptors 1 to 10 currently confirmed. In particular, lipopolysaccharides, β-glucans, double-stranded RNAs, polyinosinic-polycytidylic acid (polyIC) and anticancer agents such as taxol, defensin, heat shock proteins, fibrinogen, hyaluronic acid degradation products and so forth are preferred. PolyIC is particularly preferably used from a viewpoint of inducing and proliferating NK cells in an animal to which the NK cell proliferating drug of the present invention is administered, preferably in the peritoneal cavity of the animal. However, even Toll-like receptor ligands that have not been confirmed to date can also be used for the present invention so long as they can proliferate animal NK cells together with lactoferrin.

In the NK cell proliferating drug of the present invention, the aforementioned lactoferrin and Toll-like receptor ligand are separately packaged in the drug. In the present invention, separate packaging means that lactoferrin and a Toll-like receptor ligand are in a separated state so that they can be separately administered, and typically lactoferrin and the Toll-like receptor ligand are contained in separate containers, bags or the like. The first agent containing lactoferrin and the second agent containing a Toll-like receptor ligand are separately administered to an animal.

The aforementioned first agent is preferably administered in an amount of 10 to 2000 mg/day, more preferably 100 to 1000 mg/day, per kg body weight of an animal in terms of the amount of lactoferrin. Although the method of administration is not particularly limited, oral administration is preferred. Further, the aforementioned administration amount is preferably divided and administered one or more times per day everyday for 5 to 10 days, more preferably everyday for 7 to 8 days.

The aforementioned second agent is preferably administered in an amount of 10 to 1000 μg/day, more preferably 50 to 200 μg/day, further preferably about 100 μg/day, per kg body weight of an animal in terms of the amount of the Toll-like receptor ligand. The second agent is preferably administered as a single dose of the aforementioned amount, and a single dose of about 100 μg/kg is particularly preferably administered. Although the method of administering the second agent is not particularly limited, intraperitoneal administration is preferred. Further, the second agent is preferably administered once 5 to 2 days, preferably 3 days, before the completion of the administration of lactoferrin.

The dosage forms of the first agent and the second agent are not particularly limited so long as they are prepared to be suitable for the aforementioned administration method and schedule. Further, the first agent and the second agent may contain other ingredients that do not adversely affect storage or impair actions of these ingredients, such as carriers, excipients and pH modifiers, in addition to lactoferrin and the Toll-like receptor ligand.

The animal NK cell proliferating method of the present invention comprises administering lactoferrin and a Toll-like receptor ligand to an animal. Lactoferrin and the Toll-like receptor ligand may be the first agent and the second agent constituting the NK cell proliferating drug of the present invention, respectively.

The aforementioned animal is not particularly limited so long as NK cells are induced and proliferated by administration of lactoferrin and a Toll-like receptor ligand, and examples thereof include mouse, rat, goat, sheep, horse, bovine and so forth.

The method and schedule for administering lactoferrin and a Toll-like receptor ligand are similar to those described for the aforementioned NK cell proliferating drug of the present invention. By administering lactoferrin and a Toll-like receptor ligand, NK cells are induced and proliferated in the animal to which they have been administered. In particular, NK cells are induced in an organ or tissue to which the Toll-like receptor ligand is administered, for example, in the peritoneal cavity when the Toll-like receptor ligand is intraperitoneally administered.

The preferred timing of administration of a Toll-like receptor ligand can be determined by performing a preliminary experiment so that NK cells should be efficiently induced in an animal used. That is, a suitable condition can be determined by administering a Toll-like receptor ligand to animals to which lactoferrin is administered everyday with changing the duration from the scheduled day of the completion of the administration of lactoferrin and comparing induction of NK cells. Once a suitable condition is determined, the administration schedule can be established according to this condition when the same type of animals are used.

Proliferating of NK cells can be confirmed by, for example, using a labeled antibody that recognizes NK cells to measure the proportion of positive cells that react with the antibody among cells collected from an animal organ or tissue, for example, the peritoneal cavity. For example, when a mouse is used as the animal, an anti-CD49b/Pan-NK cell antibody (e.g., one produced by Pharmingen) can be used, and the proportion of cells positive for the CD49b/Pan-NK cell antibody can be measured to confirm NK cells. In this measurement, antigens of anti-mouse CD16/CD32 antibody or anti-rat CD32 antibody are preferably blocked by using these antibodies to reduce antibody binding via CD16/CD32 (FcγIII/II receptor) relating to the background. When C57BL/6 (strain) is used as a mouse, the proportion of NK1.1 positive cells is preferably measured by using the anti-NK1.1 antibody as an antibody that recognizes NK cells. Specifically, as described in the examples, cells can be stained by using FITC-labeled NK1.1 antibodies, and the proportion of NK1.1 positive cells can be measured by using a flow cytometer (e.g., FACS™ Calibur, Becton, Dickinson and Company).

NK cells can be prepared by collecting NK cells from an animal in which NK cells are proliferated as described above. NK cells can be collected from the animal at a time point at which NK cells are expected to be efficiently induced according to a predetermined administration schedule. After administration of lactoferrin, animals may be left for one day without administering anything, and proliferated NK cells may be collected thereafter.

NK cells can be collected in a conventional manner. For example, when NK cells are induced in the peritoneal cavity, they can be collected by washing the peritoneal cavity of the animal once or several times with a washing solution (e.g., Hank's solution) and collecting the washing solution. To purify NK cells from the washing solution containing NK cells, a method of using a cell sorter can be used, for example.

NK cells obtained by the method of the present invention are expected to maintain a high cytotoxic activity. NK cells are known to have an antiviral activity or antitumor activity. Therefore, NK cells obtained by the method of the present invention can be used for, for example, cell therapy against infection with viruses such as herpes virus and cytomegalovirus as well as the LAK (lymphokine activated killer) therapy for cancer patients.

By the present invention, it has been revealed that the NK cell proliferating action of lactoferrin was enhanced by administration of a Toll-like receptor ligand. Therefore, by using a Toll-like receptor ligand, the action of a substance having an NK cell proliferating action can be enhanced, and screening can be performed for a substance having an NK cell proliferating action with high sensitivity. That is, screening can be performed for a substance having an NK cell proliferating action by administering a test substance and a Toll-like receptor ligand to an animal and detecting induction of NK cells in the animal.

Specifically, for example, when a test substance instead of lactoferrin, and a Toll-like receptor ligand are administered to an animal according to the schedule for administration of lactoferrin determined as described above, if NK cells are induced in the animal, the aforementioned test substance is considered to have an NK cell proliferating action.

The administration method may be similar to that for the NK cell proliferating drug of the present invention. Preferably, the test substance is orally administered, and a Toll-like receptor ligand is intraperitoneally administered. Further, induction of NK cells can be detected by, for example, using a labeled antibody that recognizes NK cells and measuring the proportion of positive cells that react with the antibody as described above. For the test substance for which induction of NK cells is confirmed as described above, it is preferable to further administer the test substance alone to an animal and confirm proliferation of NK cells in an organ or tissue of the animal such as the spleen.

Examples of the preferred test substance include food and drink such as milk of animals and various components of these food and drink.

A substance having an NK cell proliferating action found by the screening method of the present invention, in particular, food or a component thereof, can be utilized as a drug, health food or a component thereof intended to be used for proliferation of NK cells or prophylactic treatment of a disease that can be prevented by proliferation of NK cells.

EXAMPLES

The present invention will be explained more specifically with reference to the following examples.

However, the scope of the present invention is not limited to these examples.

Example 1

In this example, a test was performed in order to examine the NK cell proliferating effect of lactoferrin.
(1) Test Method Forty five 7-week old C57BL/6 mice (purchased from Charles River Laboratories Japan, Inc.) were divided into 5 groups, each consisting of 9 animals, acclimatized and fed for 1 week. A solution of bovine lactoferrin (Morinaga Milk Industry Co., Ltd.) in physiological saline (Otsuka Pharmaceutical Co., Ltd.) was administered everyday to the animals of each group for 7 days in an amount of 0 (control sample), 30, 100, 300 or 1000 mg/kg body weight by using an oral sonde. After completion of the administration, the animals were left for 1 day, and the spleen was collected from each mouse, and a suspension of spleen cells was prepared. The number of cells in the prepared cell suspension was adjusted to $2\times10^6$ cells per specimen. The aforementioned cell suspension was added with 10 µl per specimen of anti-mouse CD16/CD32 monoclonal antibody (Fc Block™, Becton, Dickinson and Company) solution diluted to a concentration of 1 µg/10 µl with a Cell Wash (Becton, Dickinson and Company) solution containing 1% bovine fetal serum (henceforth referred to as "dilution buffer") and left standing on ice for 5 minutes to block the FcγIII/II receptor.

Then, the mixture was added with 10 µl of FITC-labeled anti-mouse NK1.1 antibody (Pharmingen) solution adjusted to a concentration of 1 µg/10 µl with the dilution buffer, mixed and left standing for 25 minutes to stain NK1.1 positive NK cells. Subsequently, the mixture was added with 500 µl of the dilution buffer and centrifuged at 3500 rpm for 5 minutes to wash the cells, and this washing procedure was repeated twice. Then, the cells were added with 500 µl of FACS™ Lysing Solution (Becton, Dickinson and Company) and left standing at room temperature for 10 minutes to dissolve erythrocytes. Subsequently, the cells were washed twice according to the aforementioned washing procedure, and recovered cells were added with 1 ml of the dilution buffer to prepare a cell suspension. The prepared cell suspension was filtered through a nylon screen (Flon Industry Co., Ltd., Product No.: F-3100-134) and collected in a polystyrene tube, and the proportion of NK1.1 positive cells was measured by using a flow cytometer (FACS™ Calibur, Becton, Dickinson and Company).
(2) Test Results As a result, it was found that the proportion of the NK1.1 positive cells, that is, NK cells, among the spleen cells dose-dependently increased in the administration group receiving lactoferrin in an amount of 100 to 300 mg/kg body weight.

Example 2

In this example, a test was performed in order to examine the NK cell proliferating and inducing effect of lactoferrin and a Toll-like receptor ligand.
(1) Test Method In the same manner as in Example 1, 9 mice per group, 63 mice in total, were acclimatized and fed for 1 week. Among the groups, 3 groups were assigned lactoferrin administration groups (LF groups, dose of lactoferrin: 300 mg/kg body weight/day), and the remaining 4 groups were assigned control groups (physiological saline was administered). An administration schedule was designed, in which each sample (lactoferrin or physiological saline) was administered everyday for 7 days to mice in all the 7 groups by using an oral sonde, then nothing was administered for 1 day, and the 8th day was assumed as the day of completion of the administration. Among the 3 lactoferrin administration groups and 3 groups of the control groups, groups of which mice were intraperitoneally administered with 100 μg of polyIC (Polyinosinic-Polycytidylic Acid Sodium Salt, Product No.: P-0913, Sigma) 7 days, 3 days or 1 day before completion of the administration were assigned, respectively, and the remaining one control group was assigned a group administered with no polyIC for use in the test.

After completion of the administration, 5 ml of Hank's balanced salt solution (Hank's solution "Nissui", Nissui Pharmaceutical Co., Ltd.) was injected into the peritoneal cavities of the mice in each group to wash the inside of the peritoneal cavities, this procedure was repeated twice, and the washing solution was collected to prepare intraperitoneal cell suspensions. Subsequently, in the same manner as described in Example 1, intraperitoneal cells were stained by using FITC-labeled NK1.1 antibody (Pharmingen), and the proportion of NK1.1 positive cells was measured by using a flow cytometer (FACS™ Calibur, Becton, Dickinson and Company).

(2) Test Results

The results of the above test are shown in Table 1. As a result, it was found that the proportion of NK cells and the absolute number of NK cells in the peritoneal cavity markedly increased in the group administered with polyIC 3 days before completion of the administration among the lactoferrin administration groups. However, in the other lactoferrin administration groups and control groups, significant increases were not confirmed in the proportion of NK cells or the absolute number of NK cells in the peritoneal cavities. Although increases in the proportion of NK cells and the absolute number of NK cells were confirmed in the spleens in all the 3 lactoferrin administration groups, such marked change as confirmed above in the peritoneal cavities was not confirmed.

From the above results, it was found that, under the aforementioned administration conditions, NK cells could be specifically induced in the peritoneal cavity, and the proportion and the absolute number of NK cells could be markedly increased, in particular, in the administration schedule of administering lactoferrin everyday for 7 days and completing the administration on the 8th day, by administering polyIC 3 days before completion of the administration.

TABLE 1

| Administration of polyIC | | Proportion of NK cells (%) | Number of NK cells (×$10^5$) |
|---|---|---|---|
| No administration | | 4.68 ± 0.98 | 1.58 ± 0.57 |
| | | 3.97 ± 1.84 | 1.55 ± 0.83 |
| 7 days before completion of administration | LF group | 3.77 ± 1.89 | 1.51 ± 1.06 |
| | Control group | 4.17 ± 1.88 | 1.43 ± 0.98 |
| 3 days before completion of administration | LF group | 11.28 ± 4.53* | 5.56 ± 2.45* |
| | Control group | 7.41 ± 2.70 | 1.99 ± 1.01 |
| 1 day before completion of administration | LF group | 4.89 ± 1.33 | 1.35 ± 0.63 |
| | Control group | 3.83 ± 1.81 | 0.95 ± 0.87 |

*represents significance level $p < 0.05$ in the Tukey-Kramer's test performed with respect to the control groups.

From the results of Examples 1 and 2, it was confirmed that NK cells were proliferated at least in the spleen by oral administration of lactoferrin, and that NK cells were induced in the peritoneal cavity by further intraperitoneally administering polyIC. From the above, it is considered that if another substance having an action of proliferating NK cells in a living body of an animal is administered instead of lactoferrin, and a Toll-like receptor ligand such as polyIC is, for example, intraperitoneally administered, NK cells are also induced in the peritoneal cavity. It is considered that such induction of NK cells using a substance having an NK cell proliferating action and a Toll-like receptor ligand in combination can be utilized in screening for a substance having an NK cell proliferating action.

INDUSTRIAL APPLICABILITY

Major advantages provided by the present invention are as follows.
(1) NK cells of animals including human can be specifically induced and proliferated in a large amount by administering lactoferrin and a Toll-like receptor ligand, in particular, polyIC. In this case, since NK cells are not hardly contaminated with other cell groups, improvement of the collection amount and purity of NK cells are expected in the preparation using a labeled antibody.
(2) Since NK cells can be efficiently obtained while maintaining a high cytotoxic activity, they can be utilized as a drug for cell-mediated immunity therapy such as treatment of malignant tumor or the like.
(3) Screening can be performed for a factor derived from food or drink (diet) that enhances or activates the natural killer activity (especially against virus) in vivo by oral administration without using radioactivity or special facilities.

What is claimed is:

1. A method for proliferating natural killer cells in an animal, which comprises administering lactoferrin and polyinosinic-polycytidylic acid to the animal, wherein lactoferrin is administered every day for 7 days in an amount of 10 to 2000 mg/day/kg body weight, and the polyinosinic-polycytidylic acid is administered one time at 5 days from dosage start of lactoferrin in an amount of 10 to 1000 μg/day/kg body weight.

2. The method for proliferating natural killer cells according to claim 1, wherein lactoferrin is orally administered, and the polyinosinic-polycytidylic acid is intraperitoneally administered.

3. A method for producing natural killer cells, which comprises:
   administering lactoferrin and polyinosinic-polycytidylic acid to an animal, wherein lactoferrin is administered every day for 7 days in an amount of 10 to 2000 mg/day/kg body weight, and the polyinosinic-polycytidylic acid is administered one time at 5 days from dosage start of lactoferrin in an amount of 10 to 1000 μg/day/kg body weight; and
   collecting natural killer cells from the peritoneal cavity of the animal.

4. The method for producing natural killer cells according to claim 3, wherein lactoferrin is orally administered, the polyinosinic-polycytidylic acid is intraperitoneally administered.

5. The method for proliferating natural killer cells according to claim 1, wherein the natural killer cells are proliferated in the peritoneal cavity of the animal.

* * * * *